United States Patent [19]
Bartee

[11] Patent Number: 6,019,764
[45] Date of Patent: Feb. 1, 2000

[54] METHOD OF TREATING ALVEOLAR BONE DEFECTS

[76] Inventor: Barry K. Bartee, 3234 64th St., Lubbock, Tex. 79413

[21] Appl. No.: 08/888,772

[22] Filed: Jul. 7, 1997

Related U.S. Application Data

[60] Continuation of application No. 08/585,811, Jan. 16, 1996, abandoned, which is a division of application No. 08/263,393, Jun. 20, 1994, which is a continuation-in-part of application No. 08/100,383, Aug. 2, 1993, abandoned.

[51] Int. Cl.$^7$ ...................................................... A61F 2/28
[52] U.S. Cl. .............................................................. 606/86
[58] Field of Search ................................... 606/70–76, 86

[56] References Cited

U.S. PATENT DOCUMENTS

| | | | |
|---|---|---|---|
| 4,187,390 | 2/1980 | Gore | 174/102 R |
| 4,531,916 | 7/1985 | Scantlebury et al. | 433/173 |
| 4,819,478 | 4/1989 | Melcher | 73/61.1 C |
| 4,849,285 | 7/1989 | Dillon | 428/330 |
| 4,859,383 | 8/1989 | Dillon | 264/43 |
| 5,032,445 | 7/1991 | Scantlebury et al. | 428/158 |
| 5,093,179 | 3/1992 | Scantlebury et al. | 428/158 |
| 5,196,016 | 3/1993 | Buser et al. | 606/72 |
| 5,443,483 | 8/1995 | Kirsch | 606/74 |

OTHER PUBLICATIONS

Joon Bu Park, "Biomaterials Science and Engineering" chapter 10, pp. 288 and 290, Dec. 1984.

Thomas G. Wilson, Jr., D.D.S., P.C. and Daniel Buser, D.D.S., P.D., Advances in the Use of Guided Tissue Regeneration for Localized Ridge Augmentation in Combination with Dental Implants, Texas Dental Journal 5, Jul. 7–10, 1994.

D. Buser, U. Brägger, N.P. Lang and S. Nyman, Regeneration and Enlargement of Jaw Bone Using Guided Tissue Regeneration Clin. Oral Impl. Res. 1990: 1: 22–32.

Todd V. Scantlebury, 1982–1992: A Decade of Technology Development for Guided Tissue Regeneration, J. Periodontol 1993; 64:1129–1137.

*Primary Examiner*—Michael Buiz
*Assistant Examiner*—Vy Quang Bui
*Attorney, Agent, or Firm*—Felsman, Bradley, Vaden, Gunter & Dillon, LLP

[57] ABSTRACT

A method of repairing defects in alveolar bone underlying gingival tissue by placing a layer of flexible high-density polytetrafluoroethylene (PTFE) material over the alveolar bone defect between the bone and the gingival tissue surrounding the defect. The material has a smooth surface that will not incorporate cells and will not attach to fibrous adhesions. The gingival tissue is secured over the layer of material. The alveolar bone is allowed to heal under the layer of flexible high-density polytetrafluoroethlylene (PTFE) material, and the layer of flexible high-density polytetrafluoroethylene (PTFE) material is removed with substantially no trauma to the alveolar bone and gingival tissue.

9 Claims, 8 Drawing Sheets

METHOD OF TREATING ALVEOLAR BONE DEFECTS

CROSS-REFERENCE TO RELATED APPLICATIONS

The present application is a Continuation of application Ser. No. 08/585,811, filed Jan. 16, 1996, which is a Division of application Ser. No. 08/263,393, filed Jun. 20, 1994, which is a Continuation-in-Part of application Ser. No. 08/100,383, filed Aug. 2, 1993, now abandoned.

FIELD OF THE INVENTION

This invention relates generally to devices that are used to aid in the healing process through the limitation of migration of specific cells of the body. More specifically, the invention relates to products that are placed into the body operatively or post-operatively to effect selective repopulation of cells required for the repair of bony defects.

DESCRIPTION OF THE PRIOR ART

The basic concepts which led to the clinical procedure of guided tissue regeneration were reported by Melcher in 1976 in the Journal of Periodontics. This work identified four distinct connective tissue cell phenotypes in the periodontium; the gingival corium, periodontal ligament, cementum and bone. The healing response that occurs after wounding is dependent on the phenotype of cells that repopulate the area. With the knowledge that epithelial cells from the gingiva would proliferate at a faster rate than bone or periodontal ligament cells, the early efforts at guided tissue regeneration focused on epithelial exclusion by various mechanical means. Histological evaluation of animal tissues confirmed the hypothesis that if the more aggressive and faster growing gingival epithelial cells were prevented from entering a periodontal bone defect during the healing phase, then new cementum, bone, and periodontal ligament would be formed. The concept of regeneration of the supporting tissues of the teeth and dental implants differs markedly from current therapy in which disease process may be halted, but there is no increase in overall bone mass.

At present, there is much interest in the repair and regeneration of bony defects that may result from surgery such as the removal of cysts, tooth roots or placement of dental implants, infection of teeth or dental implants, inflammatory processes around teeth or dental implants, bone atrophy, trauma, tumors or congenital defects. Such loss of bone results in pain, loss of function, mobility and subsequent loss of teeth, mobility and subsequent loss of dental implants, and recurrent infections. Additionally, deficiency of bone volume precludes adequate prosthetic reconstruction. Wound healing studies indicate that the most complete healing of oral and maxillofacial bone defects occurs when gingival epithelial and connective tissue cells are prevented from entering the bony defect.

There are several products available that are used as a barrier to block gingival epithelial and connective tissue cell migration into specific defects during the required time for preferred slower proliferating cells such as bone, cementum or periodontal ligament cells to perform a healing process. For example, one product available employs a low-density expanded version of polytetrafluoroethylene (ePTFE) which presents a open-structure matrix to the gingival epithelial and connective tissue cells. This expanded version of PTFE is characterized by a low density of about 1.0 gm/cc or less and a textured surface. Said cells readily incorporate into the matrix and connective tissue is manufactured. While this incorporation into the matrix slows the migration of said cells, it presents a difficult problem to the patient and surgeon during the removal process. After several weeks to several months, the non-absorbable low-density ePTFE barrier membrane must be removed. The incorporated cells and fibrous connective material make removal painful and traumatic to the patient and very time-consuming for the surgeon. The low-density open-matrix design of ePTFE devices also provides a location for the attachment of food particles, bacteria, and other foreign bodies which, in turn, create post-operative problems with the device such as inflammation, infection, wide exposure of the barrier material with wound dehiscence, and gingival recession which may require early removal of the barrier and compromise treatment outcome. Low-density open-matrix or open-structure materials are generally soft and flimsy such that they will not mechanically support tissue above the defect during normal activities within the mouth causing a breakdown of the barrier's effectiveness. The articles described by Scantlebury, et. al. in U.S. Pat. Nos. 5,032,445 and 4,531,916 are such ePTFE devices.

Other products available employ bio-absorbable technology into their designs. Such products are made from dense collagen matrices which resorb into the body fluids following several weeks to several months implantation. While such devices eliminate the need for a second surgical procedure to remove them, some patients may exhibit a rigorous inflammatory response to the devices which delays and often prevents the desired healing process within the defect, and may cause dehiscence of sutured wounds. The principal of bio-resorption relies on a foreign-body response to the material such that inflammation and white cell activation is required to remove the material. This foreign-body response also produces undesirable effects of retarded healing kinetics and pain. Bio-resorption time also varies significantly from patient to patient presenting both patient and surgeon with an uncertainty regarding overall healing rate and pain management. A synthetic membrane barrier exhibiting similar characteristics is Vicryl® (polyglactin) periodontal mesh. In addition, the resorbable open-structure matrix of the above mentioned products renders them susceptible to bacterial colonization.

Other products used as surgical membranes for the treatment of law and alveolar bone defects are human freeze-dried laminar bone and human freeze-dried dura mater obtained from human cadavers. These materials are bio-absorbable and osteoconductive, but carry a small but unknown risk of human disease transmission from donor to host. The risk of disease transmission precludes the use of this material by many surgeons and patients.

Particulate grafting materials such as calcium phosphates, calcium sulfates, polymers, allogenic bone, bovine bone and autogenous bone have been used as space fillers to treat bony defects. Some of these materials are claimed to be osteoconductive as well, thus facilitating selective cell repopulation of the defect, but are difficult to contain to the region of the defect. Particulate grafting materials are used as onlay grafts to improve bulk to the atrophied bone, but have the disadvantage of particle migration or exfoliation through the suture line which may lead to infection and loss of the graft. Further, autogenous bone grafting requires a second surgical site (donor site) which increases surgical morbidity.

It is thus advantageous to provide a barrier device which will provide for selective cell repopulation of bone defects that does not allow the incorporation of cells or fibrous materials, is easy to remove after extended implantation periods, will not provide a location for contamination by foreign particles or bacteria, will not elicit a foreign-body inflammatory response, does not have the potential to transmit human infectious disease, is soft and supple such that compliance is similar to soft tissues, will facilitate retention of particulate grafting materials, and is convenient to use.

SUMMARY OF THE INVENTION

The primary objective of the present invention is to provide a barrier material that will limit the migration of cells capable of causing epithelialization or fibrous healing of bony defects, provide a space for selective cell repopulation of healing bony defects, prevent the attachment of adhesions, prevent the attachment of foreign particles and bacteria, prevent a foreign body inflammatory response, preclude the transmission of human infectious disease, prevent donor site surgery, maintain a soft and supple mechanical property similar to juxtaposed soft tissues, and is convenient to use. This is accomplished by using a flexible high-density polytetrafluoroethlylene (PTFE) sheet material.

A material such as flexible high-density PTFE will not incorporate cells, and will not attach to fibrous adhesions. By presenting a smooth surface to said biological materials, the preferred invention is easily inserted and removed following extended implantation periods. The flexible property of the invention provides compliance to soft-tissues such that fibrous encapsulation is minimized.

The preferred invention will not allow passage of cells due to its high-density nature thereby limiting the migration of epithelial or connective tissue cells into the defect area. The non-reactive biocompatible chemical property of the preferred invention prevents a foreign-body inflammatory response. This property allows for normal healing kinetics and overall comfort to the patient during the implantation period. Further, the synthetic nature of the preferred invention precludes the transmission of human infectious disease.

The present invention consists of a flexible sheet of polymeric tape, rectangular in shape, and of convenient size. The tape may be cut and shaped by the surgeon as required for a specific defect without changing the desirable properties of the tape. If desired, the present invention may be shaped into a semi-cylindrical shape to approximate the preferred shape of the outer-surface of the healed bony defect. This configuration will allow the surgeon to pre-determine the final shape of the totally healed defect by pre-shaping the preferred invention and thereby providing protection for the underlying blood clot which contains the correct elements for the desired bone healing and/or periodontal regeneration.

The present invention may be wrapped around a tooth or implant abutment to prevent the migration of gingival epithelial and connective tissue cells apically into the periodontal or perimplant osseous defect or osteotomy. The flexible and conformable properties of the preferred invention allow the surgeon to easily shape and tighten the preferred polymeric tape around the tooth or implant abutment such that epithelial cell migration and contamination by food particles and bacterial is prevented during normal mouth activity. The preferred invention may be secured by placement under mucoperiosteal flaps with suture, adhesives, screws, or other mechanical or chemical means.

The present invention may be used to prevent the migration or loss of graft material placed into the bony defect or osteotomy such as ceramic and metallic dental implants, natural or synthetic hydroxylapatite granules, bone replacement polymers, calcium sulphite bone autografts or allografts, hemostatic agents, drug delivery systems, or polypeptide growth factor delivery systems which may be placed into such defects without mechanism for primary retention. The polymeric tape provides a retentive cover over the implanted material during the healing process.

The successful placement of oral implant fixtures is based upon bony integration with the implant surface without an intervening soft tissue layer. This soft tissue layer formation is prevented by the creation of a tight fit with implant body and bone, and by protecting the implant body from stress or movement for at least 12 weeks following placement. At surgery, there are a host of factors which may in fact prevent a tight bone-implant interface along the entire length of the implant. First among these is a so called fenestration defect that occurs on the lateral surface of the jaw bone when the implant drill, which may be slightly larger than the bone or due to angulation of the bone is directed in a lateral fashion, create a secondary opening which will be covered with soft tissue at the end of surgery. Many of these fenestration injuries have led to early loss of dental implants with resultant cost and morbidity. Secondly, there can be incomplete bony coverage of the implant body at the time of surgery due to insufficient bony depth or width at the crest of the bony ridge. This type of defect can lead to early crestal bone Loss around the implant neck and subsequent disease. It has been shown that membrane barriers which provide space for bone healing to occur and which prevent soft tissue cell migration to occur can significantly enhance surgical outcome in areas of bony deficiency. Moreover, it has been shown that low-density open-structure properties of these membranes lead to complications with the barrier which may require its removal, and allow migration of soft tissue cells through the barrier resulting in reduced bony healing.

Oral implant treatment can be a very lengthy process. A patient presenting with diseased teeth and gums will require one surgical procedure to remove the diseased teeth, after which, at least 6–12 weeks of healing must occur before the implants can be placed. During this healing time the patient must be maintained in a temporary prosthesis with no internal support. Then following the implant placement, the patient must heal for a minimum of 12 weeks before the teeth can be secured. Due to a desire to shorten the overall treatment time there have been attempts to place oral implants into fresh extraction sites. This procedure has two major problems associated with it. First, there is insufficient bony contact with the implant body to prevent soft tissue ingrowth around the implant which compromises healing. Second, there is always insufficient soft tissue to effect primary or complete closure over the implant body, thus exposing the implant surface salivary, food and bacterial contamination. This often results in infection and early implant removal. Of the implants that do survive there is often a deficiency of bone at the neck of the implant which compromises long term results. Efforts to evaluate the effects of barrier membranes in conjunction with oral implants are showing promising results. However, the low-density open-structure membranes currently in use can create complications related to bacterial contamination or cellular infiltration beneath the barrier.

The present invention may be readily used by those skilled in the art to cover these fenestration defects, provide a space-maker to encourage bone height at the neck of oral implants and as a barrier over implant placed into fresh extraction sites to facilitate bony integration of the implant by exclusion of soft tissue, prevention of bacterial and foreign body contamination of the wound, and reduction in the amount of resorption of the healing extraction site.

The advantages of the present invention are readily apparent and additional advantages will become apparent from the accompanying drawings.

DESCRIPTION OF THE PREFERRED EMBODIMENT

Figure 1:
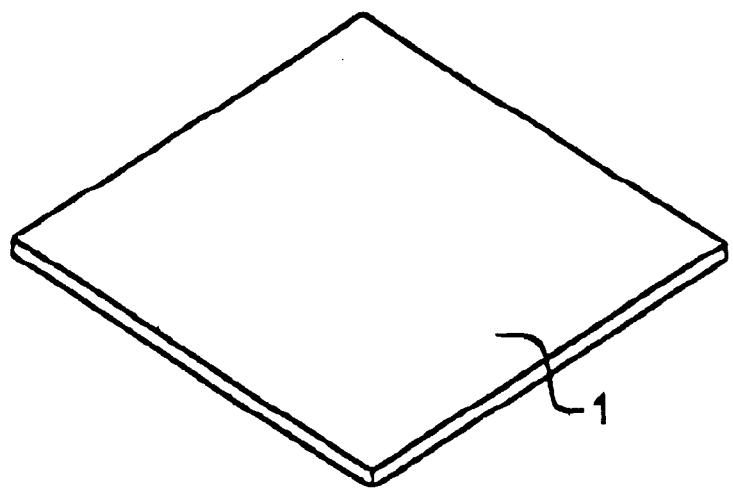
FIG. 1 is a three dimensional view of the present invention.

The present invention is generally shown as reference 1 in FIG. 1. The device is shown as a flat polymeric sheet of a convenient size. The device may be cut, perforated, and shaped as the surgeon desires for a specific case without changing the desirable properties of the invention.

Figure 2:
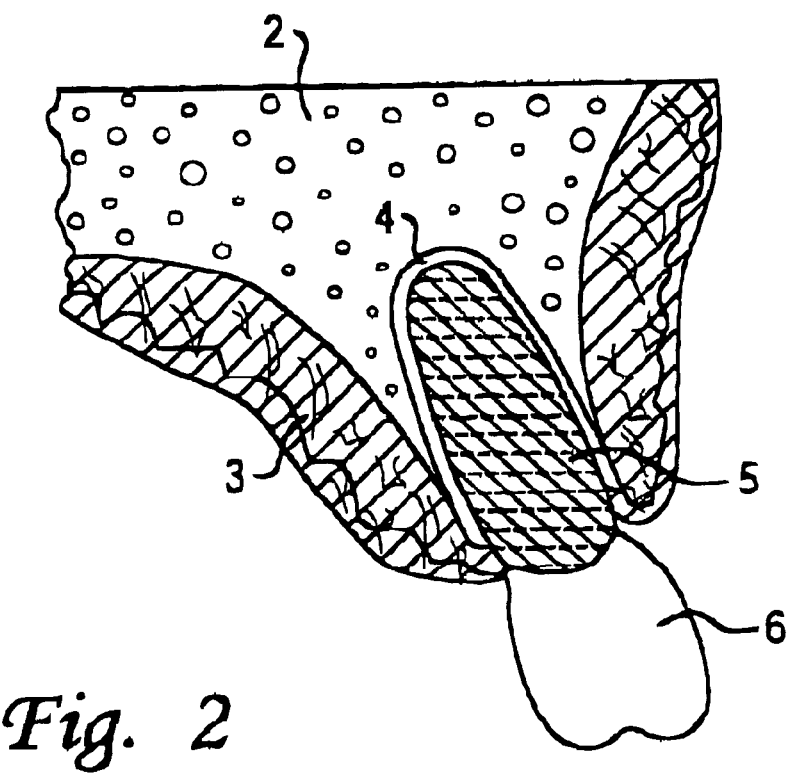
FIG. 2 is a lateral cross-sectional view of an adult human maxilla prior to tooth extraction.

FIG. 2 is a lateral cross sectional view of adult human maxilla showing the bone 2 of the alveolar process. Soft tissue gingiva 3 covers said bone and protects the cementum/periodontal membrane 4 and tooth root 5. The protruding tooth crown is shown as reference 6. Periodontal disease begins when bacterial contamination causes a breakdown in the epithelial attachment resulting in a deepening of the gingival sulcus. This pocket formation allows further accumulation of bacteria and subsequent breakdown of the periodontal ligament, cementum and supporting bone. Advanced stages of said disease resulting in progressive mobility of the tooth and eventual tooth loss, and overall bone mass loss to the alveolar process.

Figure 3:
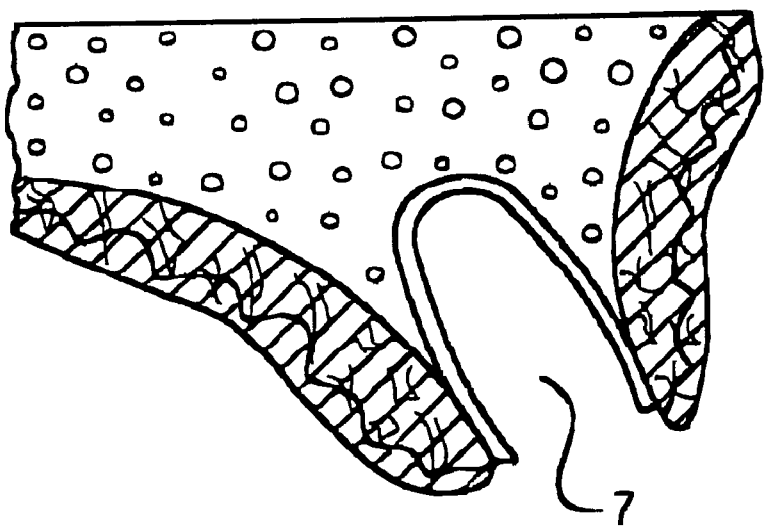
FIG. 3 is a lateral cross-sectional view of the maxillary bony defect resulting following tooth extraction.

FIG. 3 depicts a lateral cross-sectional view of a resultant bony defect (cavity) 7 following tooth extraction. Normal healing of this defect includes migration of foreign cells such as fibroblasts and gingival epithelial cells. As said cells proliferate into the bony defect, they inhibit bone cell regeneration resulting with overall loss of bone mass.

Figure 4:
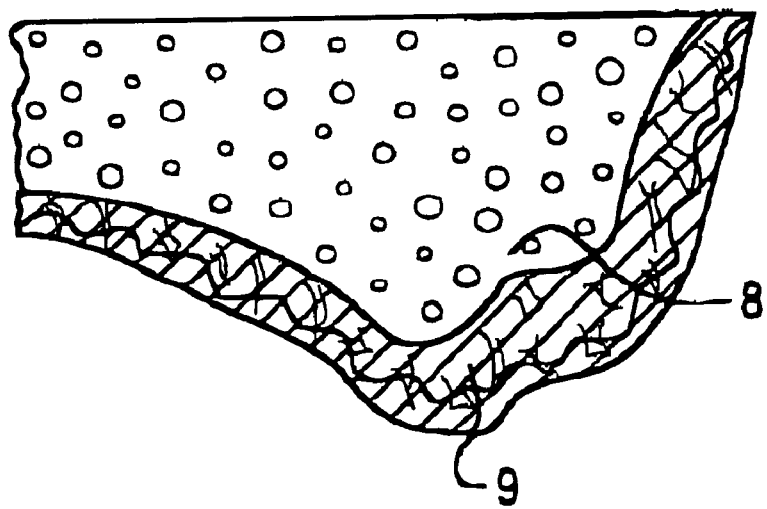
FIG. 4 is a lateral cross-sectional view of a normally healed bony defect showing overall decreased bone mass.

FIG. 4 shows the healed cross sectional-view of a bony defect depicting bone loss 8 and subsequent overall loss to the alveolar ridge profile 9. This loss of ridge profile presents the patient and surgeon with a problem when later attempting to secure prosthetic tooth appliances such as a denture plate. Prosthetic devices resting on extremely resorbed alveolar ridges are inherently unstable, resulting in dysfunction and discomfort for the patient. Thus it is highly desirable to prevent alveolar bone resorption following extraction of teeth.

Figure 5:
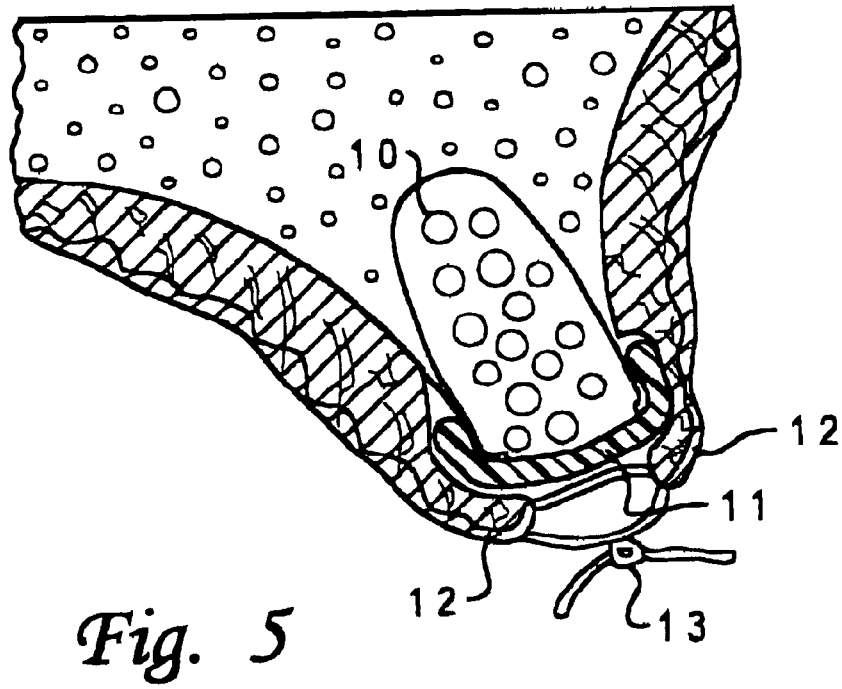
FIG. 5 is a lateral cross-sectional view of an adult maxilla following tooth extraction and placement of the preferred invention as a cover over the defect with the mucoperiosteal flap sutured in position.

FIG. 5 shows a lateral cross-sectional view of an adult maxilla following tooth extraction and placement of the preferred invention. The bony defect or cavity is packed with granular particles of hydroxyapatite 10 as a precursor to bone and the packed cavity is covered with the preferred invention 11. Suture 13 is used to stay the preferred invention by holding the gingival flaps 12 over said invention. The preferred invention 11 holds the loosely packed particles 10 into the cavity during the healing process and also prevents gingival epithelial cell migration into the cavity and gingival connective tissue migration. This grafting process results in a marked decrease in bone loss during the healing process due to promotion of bony healing.

Figure 6:
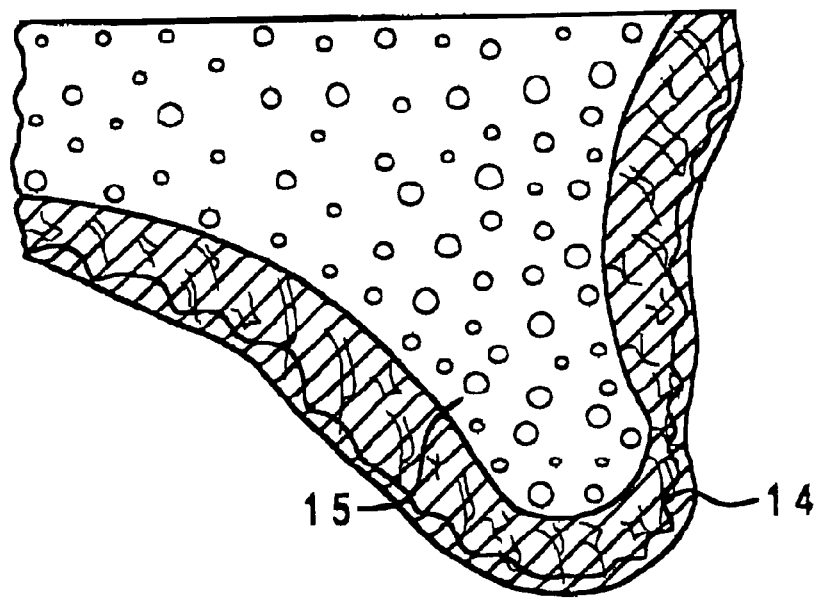
FIG. 6 is a lateral cross-sectional view of an adult maxilla healed following removal of the preferred invention showing no significant bone loss.

FIG. 6 depicts a lateral cross-sectional view of an adult maxilla totally healed following removal of the preferred invention. New alveolar bone mass has replaced the bony defect or cavity. A new gingival epithelial cap 14 covers the healed bony defect.

Figure 7:
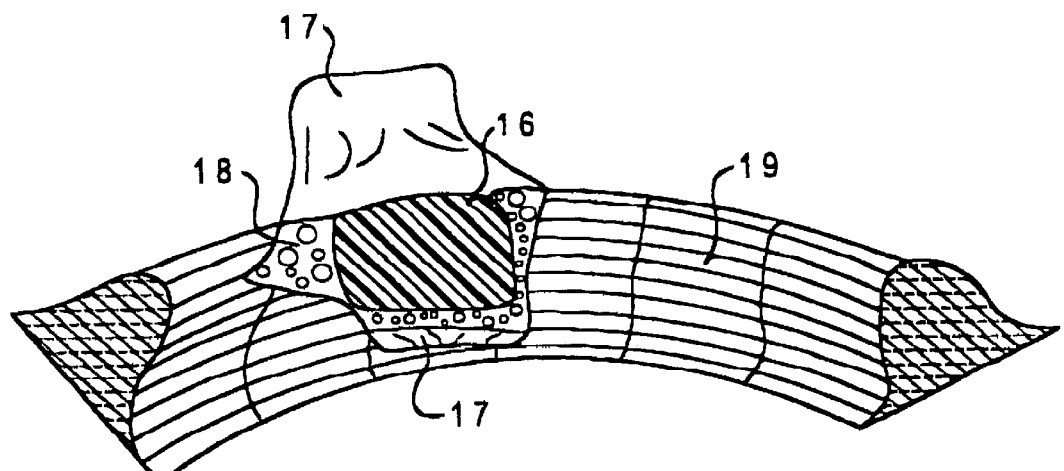
FIG. 7 is a three dimensional view of the human jaw depicting placement of the preferred invention over a bony defect and under mucoperiosteal flaps.

FIG. 7 is a three dimensional view of an adult jaw depicting the alveolar process 19. The preferred invention 16 is shown inserted under the retracted gingival flaps 17 and adjacent to the bone 18. To close the wound, the surgeon places the gingival flaps and periosteum 17 over the preferred invention and stays the flaps with suture.

Figure 8:
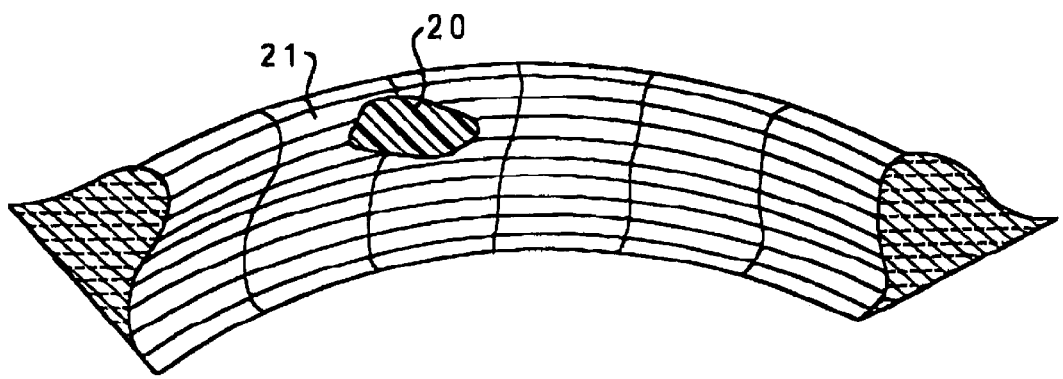
FIG. 8 is a three dimensional view of the human jaw depicting a healing osseous and mucoperiosteal defect with the preferred invention in place.

FIG. 8 is a three dimensional view of an adult jaw depicting the alveolar process 21. The preferred invention 20 is shown implanted beneath gingival tissue and healing is progressing with epithelial cell migration over the superior surface of the preferred invention.

Figure 9:
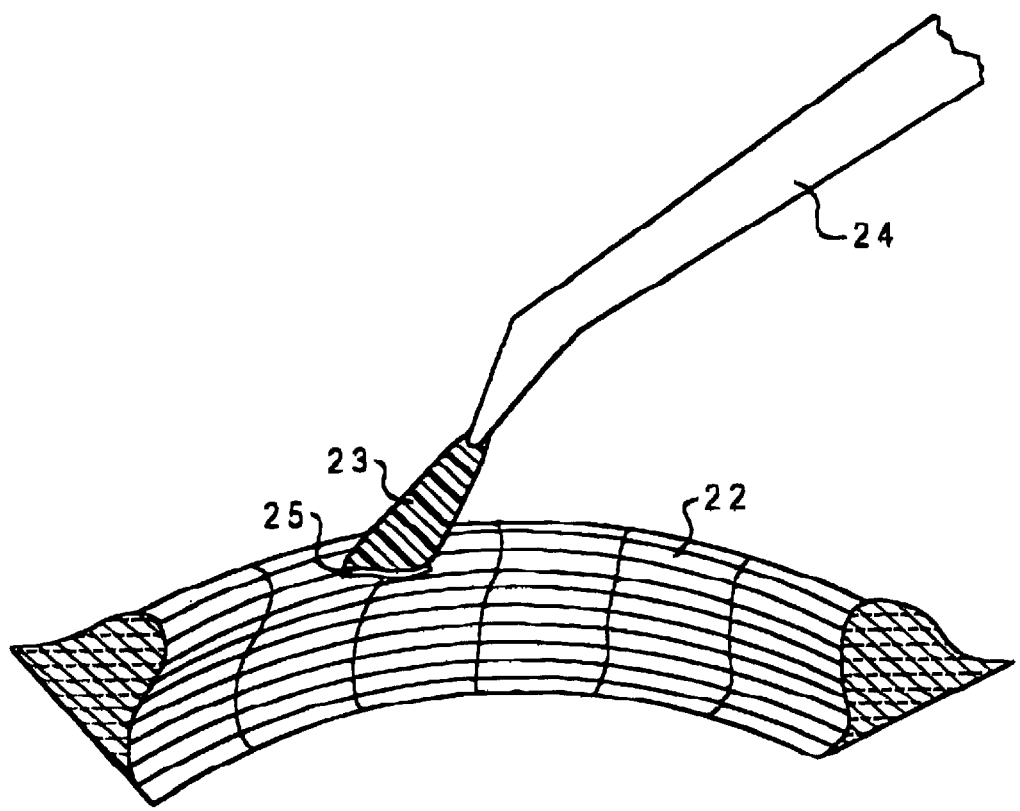
FIG. 9 is a three dimensional view showing removal of the present invention with forceps from a healed extraction site.

FIG. 9 is a three dimensional view of an alveolar process 22 depicting the removal of the preferred invention 23 through a small incision in the gingiva with a forceps 24. The preferred invention is easily removed with little or no trauma to the gingival tissues or bone.

Figure 10:
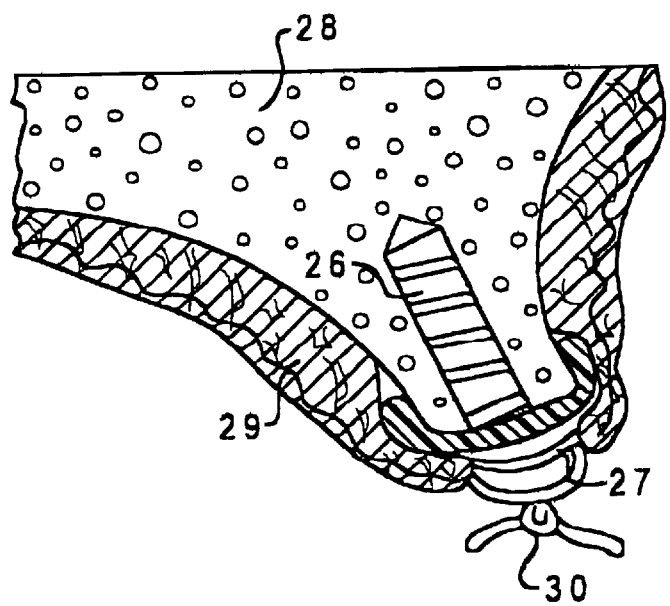
FIG. 10 is a lateral cross-sectional view of the present invention placed over an root-form implant body.

FIG. 10 shows a lateral cross-sectional view of the present invention 27 covering an implant body 26. The preferred invention 27 is placed adjacent to alveolar bone 28 and under the gingival tissues and periosteum 29 which are stayed with suture 30. The present invention prevents migration of gingival epithelium and connective tissue into the interface between the implant and bone, facilitating direct bony healing of the implant. In addition, the space-making capabilities of the preferred invention allow for additional bone generation in deficient or thin areas.

Figure 11:
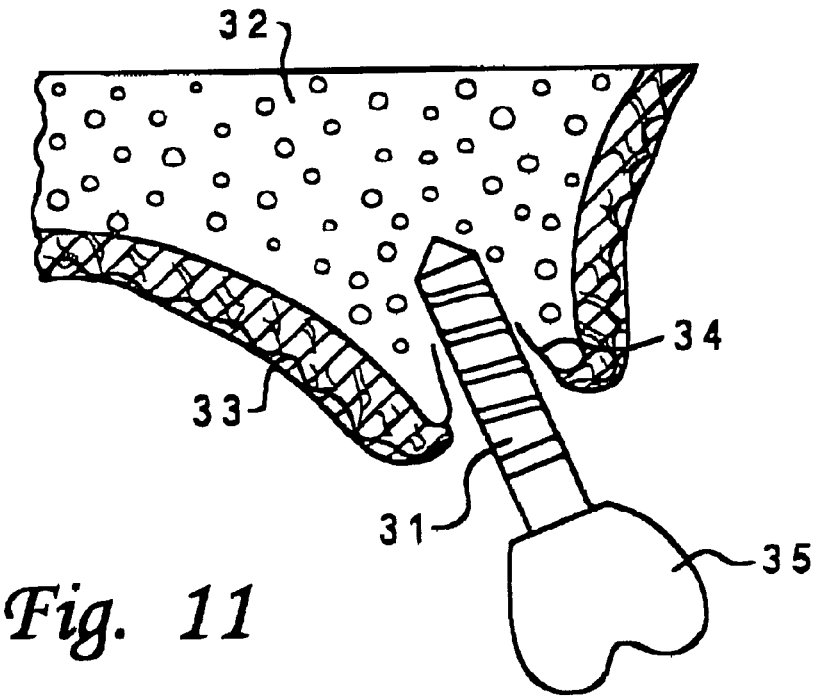
FIG. 11 is a lateral cross-sectional view of a human jaw depicting bone loss adjacent to an implant resulting from occlusal overloading (stress) around said root-form dental implant.

FIG. 11 shows a lateral cross-sectional view of an adult jaw depicting bone loss due to implant stress and/or bacterial infection. The alveolar bone 32 anchors the distal end of the implant body 31 which supports the implant prosthetic tooth crown 35. Pockets 34 have been formed due to bone loss resulting in overall loosening of the implant assembly. Gingival tissue 33 has also receded away from the implant due to contamination such as food, bacteria, and foreign particles becoming lodged in said pockets 34 which leads to further progression of bone and tissue loss if untreated.

Figure 12:
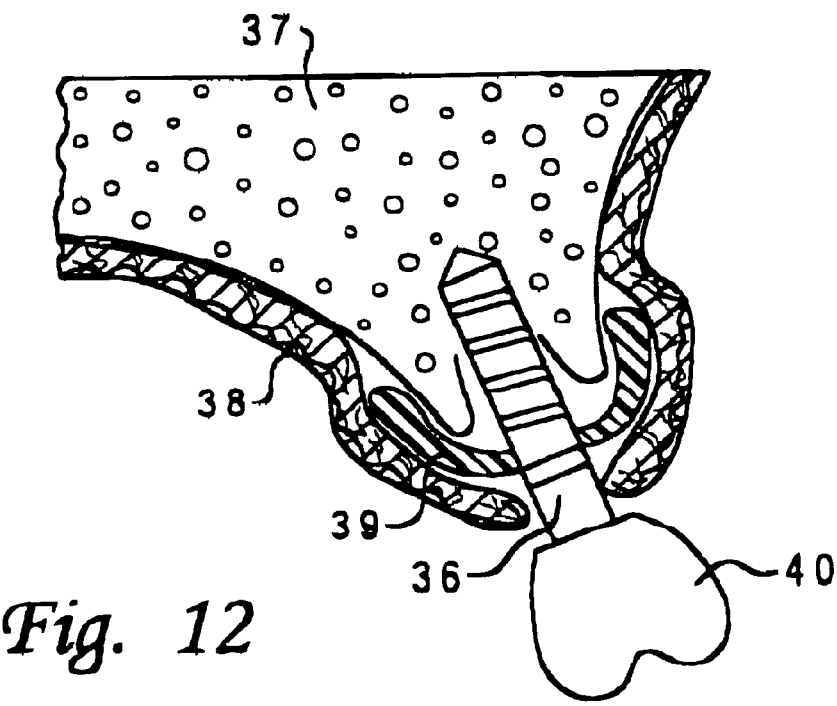
FIG. 12 is a lateral cross-sectional view of the present invention placed around an implant to facilitate bone regeneration and healing.

FIG. 12 depicts a lateral cross-sectional view of the preferred invention 39 placed around the implant body 36 and adjacent to the alveolar bone 37. The preferred invention 39 is placed under gingival epithelium and periosteum 38. The prosthetic tooth crown 40 is anchored to the implant body 36 and may be removed during the early healing phase to decrease stress transmission to the underlying bone.

Figure 13:
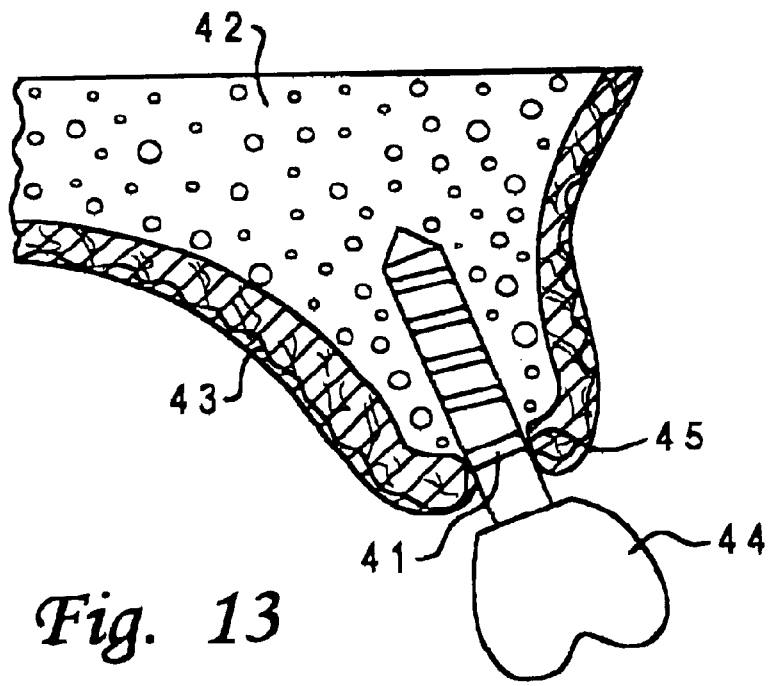
FIG. 13 is lateral cross-sectional view of a human jaw following removal of the preferred invention showing a totally healed bony defect adjacent to the implant.

FIG. 13 depicts a lateral cross-sectional view of a healed human jaw following removal of the preferred invention showing healthy alveolar bone 42 without pockets and tightly juxtaposed 45 to the implant body 41 and prosthetic tooth crown 44 assembly. Healthy gingival tissue and connective tissue 43 has healed adjacent to the implant provides protection for the newly formed bone.

Figure 14:
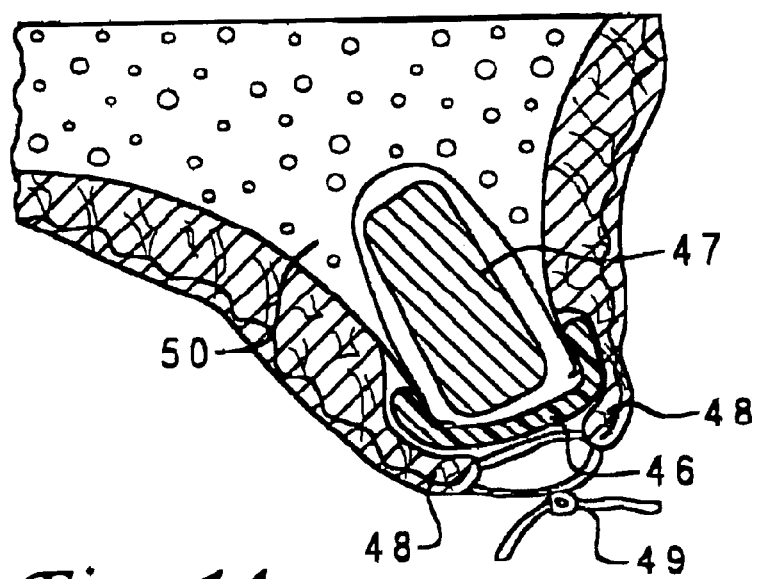
FIG. 14 is a lateral cross-sectional view of a human jaw depicting the preferred invention placed over a fresh extraction site containing a dental implant.

FIG. 14 depicts a lateral cross-sectional view of a human jaw showing the preferred invention 46 placed over a fresh extraction site. A dental implant 47 is shown protected by said invention 46 placed as a cap over the implant and any grafting material protecting said material from migrating out and away of the defect and keeping gingival epithelial cells out of said defect. The preferred invention 46 is placed tightly against the alveolar bone 50 and under gingival flaps 48 which are stayed by suture 49.

Figure 15:
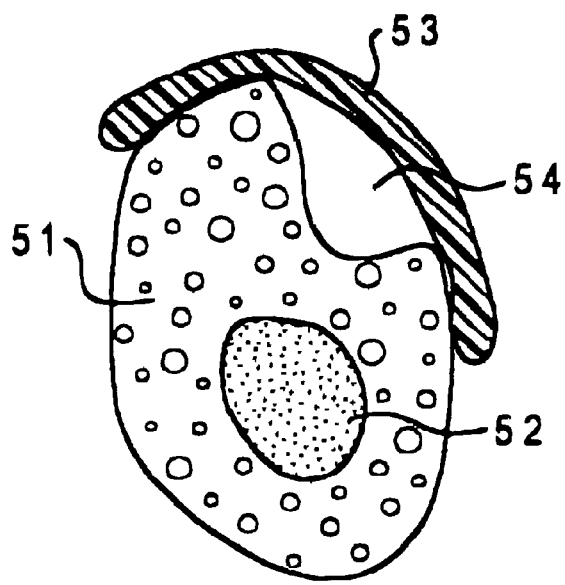
FIG. 15 is a lateral cross-sectional view of an adult skeletal bone depicting the preferred invention placed as a space-maker providing for augmentation of a bony defect.

A lateral cross-sectional view of an adult skeletal bone 51 and corresponding bone marrow 52 is depicted by FIG. 15. The preferred invention 53 is placed as a space-maker over a bony cavity 54. This configuration of said invention 53 provides for augmentation of said bone 51 allowing reconstruction of homogeneous bone into the said space 54.

Figure 16:
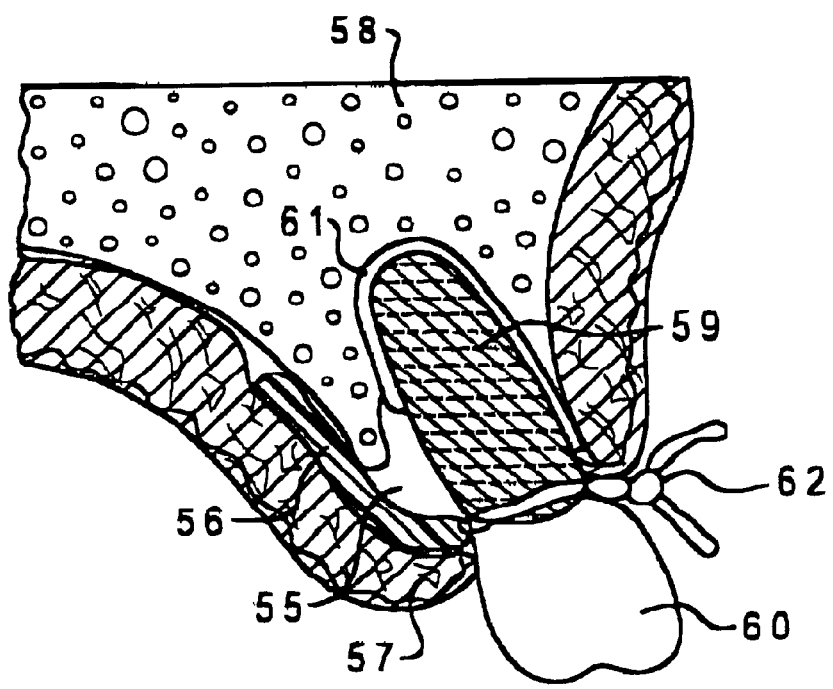
FIG. 16 is a lateral cross-sectional view of a human jaw depicting the preferred invention placed over a periodontal defect adjacent to a tooth root.

The lateral cross-sectional view of a human jaw depicted by FIG. 16 shows the preferred invention 56 placed over a pocket defect 55 formed as the result of periodontal disease. The pocket defect 55 results firstly from loss of periodontal ligament and cementum 61 followed by loss of alveolar bone 58. The preferred invention 56 is tightly juxtaposed against the tooth root 59 and tooth crown 60 and under a gingival flap 57 to prevent gingival epithelial cell migration into the defect. This tight juxtaposition of said invention 56 which is held secure by suture 62 prevents contamination of the defect by bacteria, food particles, and other foreign body debris.

What is claimed is:

1. A method of preserving alveolar ridge profile following the extraction of a tooth, which comprises the steps of:
   placing a layer of flexible high-density polytetrafluoroethlylene (PTFE) material, said material having a density from about 1.6 gm/cc to about 2.3 gm/cc and having a smooth surface that will not incorporate cells and will not attach to fibrous adhesions, over the tooth extraction site between the bone and the gingival tissue surrounding the extraction site;
   at least partially closing the gingival tissue over the material;
   allowing the alveolar bone to heal under the layer of flexible high-density polytetrafluoroethlylene (PTFE) material; and,
   removing the layer of flexible high-density polytetrafluoroethlylene (PTFE) material.

2. The method as claimed in claim 1, including the step of:
   filling the extraction site with particulate grafting material prior to placing the layer of flexible high-density polytetrafluoroethlylene (PTFE) material.

3. The method as claimed in claim 1, including the steps of, prior to placing the layer of flexible high-density polytetrafluoroethlylene (PTFE) material:
   placing an endoceouss-type dental implant into the extraction site;
   filling the extraction site around the implant with particulate grafting material.

4. The method as claimed in claim 1, wherein said step of removing the layer of flexible high-density polytetrafluoroethlylene (PTFE) material includes the steps of:
   making an incision in the gingival tissue to expose a portion of the layer of flexible high-density polytetrafluoroethlylene (PTFE) material;
   grasping the exposed portion; and,
   pulling the layer of flexible high-density polytetrafluoroethlylene (PTFE) material through the incision with substantially no trauma to the alveolar bone and gingival tissue.

5. The method as claimed in claim 4, wherein said incision is smaller than the layer of flexible high-density polytetrafluoroethlylene (PTFE) material.

6. A method of treating pocket defects in the alveolar bone adjacent a tooth or dental as a result of periodontal disease, which comprises the steps of:
   placing a layer of flexible high-density polytetrafluoroethlylene (PTFE) material, said material having a density from about 1.6 gm/cc to about 2.3 gm/cc and having a smooth surface that will not incorporate cells and will not attach to fibrous adhesions, around the tooth or dental implant and over the pocket defect between the bone and the gingival tissue surrounding the pocket;
   securing the gingival tissue over the material;
   allowing the alveolar bone to heal under the layer of flexible high-density polytetrafluoroethlylene (PTFE) material; and,
   removing the layer of flexible high-density polytetrafluoroethlylene (PTFE) material.

7. The method as claimed in claim 6, wherein said step of removing the layer of flexible high-density polytetrafluoroethlylene (PTFE) material includes the steps of:
   making an incision in the gingival tissue to expose a portion of the layer of flexible high-density polytetrafluoroethlylene (PTFE) material;
   grasping the exposed portion; and,
   pulling the layer of flexible high-density polytetrafluoroethlylene (PTFE) material through the incision with substantially no trauma to the alveolar bone and gingival tissue.

8. A method of repairing a defect in alveolar bone underlying gingival tissue, which comprises the steps of:
   placing a layer of flexible high-density polytetrafluoroethlylene (PTFE) material, said material having a density from about 1.6 gm/cc to about 2.3 gm/cc and having a smooth surface that will not incorporate cells and will not attach to fibrous adhesions, over the alveolar bone defect between the bone and the gingival tissue surrounding the defect;
   securing the gingival tissue over the layer of material;
   allowing the alveolar bone to heal under the layer of flexible high-density polytetrafluoroethlylene (PTFE) material; and,
   removing the layer of flexible high-density polytetrafluoroethlylene (PTFE) material.

9. The method as claimed in claim 10, wherein said step of removing the layer of flexible high-density polytetrafluoroethlylene (PTFE) material includes the steps of:

making an incision in the gingival tissue to expose a portion of the layer of flexible high-density polytetrafluoroethlylene (PTFE) material;

grasping the exposed portion; and, pulling the layer of flexible high-density polytetrafluoroethlylene (PTFE) material through the incision with substantially no trauma to the alveolar bone and gingival tissue.

* * * * *